(12) United States Patent
Yoshida (10) Patent No.: US 11,161,671 B2
(45) Date of Patent: Nov. 2, 2021

(54) MEDICAL DEVICE CONTAINER

(71) Applicant: DAIKYO SEIKO LTD., Sano (JP)

(72) Inventor: Takayuki Yoshida, Sano (JP)

(73) Assignee: DAIKYO SEIKO LTD., Sano (JP)

( * ) Notice: Subject to any disclaimer, the term of this patent is extended or adjusted under 35 U.S.C. 154(b) by 91 days.

(21) Appl. No.: 16/487,968

(22) PCT Filed: Jul. 18, 2019

(86) PCT No.: PCT/JP2019/028194
§ 371 (c)(1),
(2) Date: Aug. 22, 2019

(87) PCT Pub. No.: WO2021/009890
PCT Pub. Date: Jan. 21, 2021

(65) Prior Publication Data
US 2021/0016950 A1    Jan. 21, 2021

(51) Int. Cl.
*B65D 81/20* (2006.01)
*B65D 25/10* (2006.01)
*A61J 1/16* (2006.01)

(52) U.S. Cl.
CPC ............ *B65D 81/2015* (2013.01); *A61J 1/16* (2013.01); *B65D 25/108* (2013.01)

(58) Field of Classification Search
CPC .............. B65D 25/108; B65D 81/2015; B65D 81/2076; A61J 1/16
USPC ..... 206/363–369, 438, 497, 499, 524.8, 557
See application file for complete search history.

(56) References Cited

U.S. PATENT DOCUMENTS

| | | | | |
|---|---|---|---|---|
| 6,164,044 A * | 12/2000 | Porfano | ................. | B65B 55/10 422/28 |
| 7,100,768 B2 * | 9/2006 | Grimard | ................. | A61L 2/183 206/438 |
| 8,100,263 B2 * | 1/2012 | Vanderbush | ............ | B65B 5/067 206/524.8 |
| 9,783,328 B2 * | 10/2017 | Liversidge | ............ | A61M 5/008 |
| 2005/0214924 A1 * | 9/2005 | Glaser | .................... | C12M 23/48 435/252.1 |
| 2008/0173563 A1 * | 7/2008 | Perot | ...................... | A61B 50/20 206/438 |

(Continued)

FOREIGN PATENT DOCUMENTS

| | | |
|---|---|---|
| DE | 10301386 A1 | 11/2003 |
| DE | 102008046378 A1 | 3/2010 |

(Continued)

OTHER PUBLICATIONS

PCT/ISA/210, "International Search Report for International Application No. PCT/JP2019/028194," dated Aug. 27, 2019.

(Continued)

*Primary Examiner* — Luan K Bui
(74) *Attorney, Agent, or Firm* — Manabu Kanesaka (57) ABSTRACT

To provide a medical device container, which enables transportation of a stored medical device in a fixed condition. A medical device container includes a container body having an opening portion at the upper portion; a holder, which is housed in the container body, for holding at least one medical device; and a gas non-permeable film sealing the opening portion of the medical device container; wherein the internal pressure of the medical device container is set to a value less than the atmospheric air pressure.

13 Claims, 9 Drawing Sheets

(56) References Cited

U.S. PATENT DOCUMENTS

| | | | | |
|---|---|---|---|---|
| 2009/0095647 | A1* | 4/2009 | Togashi | A61M 5/008 |
| | | | | 206/438 |
| 2014/0353190 | A1* | 12/2014 | Okihara | B65D 1/22 |
| | | | | 206/370 |
| 2015/0182686 | A1* | 7/2015 | Okihara | A61B 50/22 |
| | | | | 206/366 |
| 2017/0348476 | A1* | 12/2017 | Thompson | B65D 71/70 |
| 2018/0126066 | A1* | 5/2018 | Narvekar | B65B 43/54 |
| 2018/0207308 | A1* | 7/2018 | Okihara | A61J 1/00 |

FOREIGN PATENT DOCUMENTS

| | | |
|---|---|---|
| EP | 2 818 190 A1 | 12/2014 |
| JP | H01-164368 A | 6/1989 |
| WO | 2013/125443 A1 | 8/2013 |

OTHER PUBLICATIONS

PCT/ISA/237, "Written Opinion of the International Searching Authority for International Application No. PCT/JP2019/028194," dated Aug. 27, 2019.

\* cited by examiner

MEDICAL DEVICE CONTAINER

RELATED APPLICATIONS

The present application is National Phase of International Application No. PCT/JP2019/028194 filed Jul. 18, 2019, the disclosure of which is hereby incorporated by reference herein in its entirety.

TECHNICAL FIELD

The present invention relates to a medical device container which can transfer a stored medical device in a fixed condition.

BACKGROUND ART

For transferring a medical device, it is known to use a container for housing a medical device in a container body and packaging an opening portion of the container body by a gas non-permeable film or a film composed of a high density polyethylene no-woven cloth like "Tyvek (Registered Trademark)" made by DuPont (hereinafter, it may be referred to as "Tyvek and the like") through which gas permeates but bacteria does permeate. For example, WO2013/125443A1 (Patent Document 1) proposed a container for housing a medical device in a container body and packaging an opening of the container body by "Tyvek and the like."

However, it is impossible to transfer a stored medical device in a fixed condition by a packaging form using only such "Tyvek and the like", and there is a risk of degrading the cleanliness of the medical device by a movement of the holder for storing the medical device and a risk of dropping the medical device from the holder. It was also worried about an occurrence of a trouble like a stoppage of an automated eject machine for ejecting a medical device at a transport destination and others which may be caused by a misalignment of the medical device.

PRIOR ART DOCUMENT

Patent Document
Patent Document 1: WO2013/125443A1

DISCLOSURE OF INVENTION

Problems to be Resolved by the Invention

In order prevent such a problem, when an opening portion of a container body is packaged by "Tyvek and the like", a medical device is fixed by a reduced pressure package (hereinafter, it may be referred to as "a vacuum bag package") which is performed by vacuuming after putting the entire part of the medical device container in a bag-shaped member.

However, because the internal pressure of the vacuum bag package changes depending upon the condition of setting it to a vacuum sealing machine by an operator, it is difficult to control the internal pressure of the vacuum bag package to a constant value and therefore the internal pressure varies widely. As the medical device container is shipped to pharmaceutical companies or medical agencies, it is necessary, in general, to remove the vacuum bag package and then remove a cover which sealed the opening portion of the container in a sterile atmosphere at the delivered sites, and the operation requires great care. Especially, when a medical agent is filled in the medical device using a filling machine by an automated process, it was not easy to remove the vacuum bag package in such a process.

Therefore, the task of the present invention is to provide a medical device container which can transfer a stored medical device in a fixed condition without vacuum bag packaging. Furthermore, the task of the present invention is to provide a medical device container which enables an easy removal of the package even during an automated process in a filling machine for filling a medical agent and the like in the medical device.

Means for Solving the Problems

The inventor of the present invention studied hard to resolve the above-mentioned problem. Consequently, the following invention was made.

(1) A medical device container comprising a container body having an opening portion at its upper portion and housing a holder for holding at least one medical device, wherein the opening portion is sealed by a gas non-permeable film and the internal pressure of the medical device container is set to a value which is less the atmospheric air pressure.

(2) A medical device container described in (1), wherein the gas non-permeable film contacts the medical device and/or the holder.

(3) A medical device container described in (1) or (2), wherein the ratio ($\alpha/L$) is set to $0 < \alpha/L \leq 0.15$, where L is the longitudinal length of a basial plate portion of the holder, and $\alpha$ is the maximum displacement of the basial plate portion of the container in a vertical direction toward the bottom surface of the container body.

(4) A container for a medical device for a medical device described in either one of (1) through (3), wherein the ratio ($M1/M2$) is set to $0.70 \leq M1/M2 \leq 0.99$, where M1 is the area of the opening portion of the container body before the pressure reduction, and M2 is the area of the gas non-permeable film which seals the opening portion before the pressure reduction.

Effect of Invention

In a medical device container according to the present invention, a stored medical device can be transferred in a fixed condition without vacuum bag packaging. Furthermore, it is possible to remove the package easily by an automated process in a filling machine for filling a medical agent or the like.

BRIEF DESCRIPTION OF DRAWINGS

FIG. 2 (A) shows a plan view of the medical device container shown in FIG. 1; and (B) shows a cross-section view of the container shown in (A) which is cut along the line 2(B)-2(B).

FIG. 5 (A) shows an enlarged perspective view of the holder shown in FIG. 4(A) and (B); (B) shows an enlarged front view of the holder shown in (A); and (C) shows a front view of a cap (medical device) held in the holder.

FIG. 7 (A) shows a partial enlarged view of the holder shown in FIG. 6; and (B) shows an enlarged cross-section view of a condition where a vial is held in the holder shown in (A).

FIG. 9 (A) shows a perspective view of a gas non-permeable film in a condition where the center portion sags; and (B) shows a cross-section view of the film shown in (A) which is cut along the line 9(B)-9(B).

A MODE FOR IMPLEMENTING THE INVENTION

Figure 1:
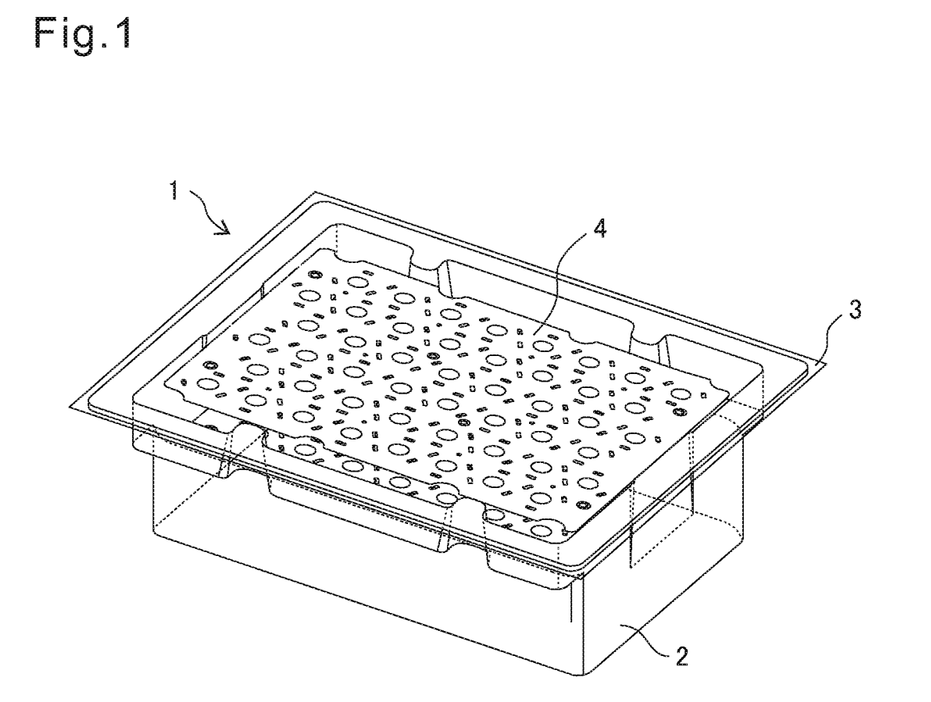
FIG. 1 shows a perspective view of one embodiment of a medical device container according to the present invention.
Figure 2A:
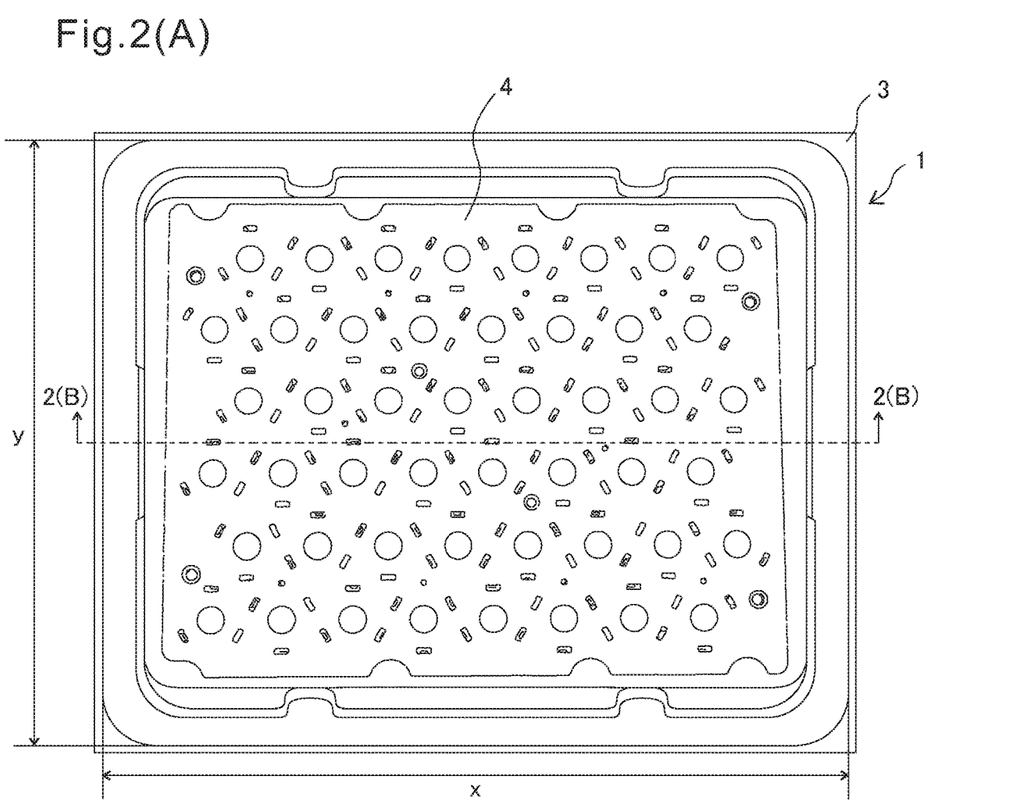
Figure 2B:
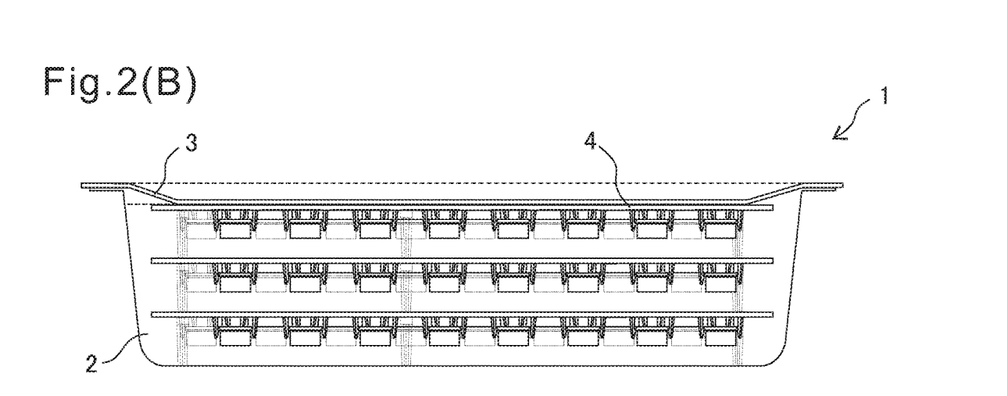

[Embodiment] One embodiment according to the present invention will be explained below referring to FIGS. 1 through 9. FIG. 1 shows a perspective view of one embodiment of a medical device container 1 according to the present invention; and FIG. 2 (A) shows a plan view of the medical device container 1 shown in FIG. 1, and (B) shows a cross-section view of the medical device container shown in (A) which is cut along the line A-A. As shown in FIG. 1 and FIG. 2(A) (B), the medical device container 1 according to this embodiment comprises a container body 2 having an opening at the upper portion, a medical device holder 4 which is housed in the container body 2 and a gas non-permeable film 3 for sealing the opening portion at the upper portion of the container body 2, wherein the internal space of the medical device container 1 is kept in a reduced pressure condition where the pressure is less than the atmospheric air pressure.

Figure 3:
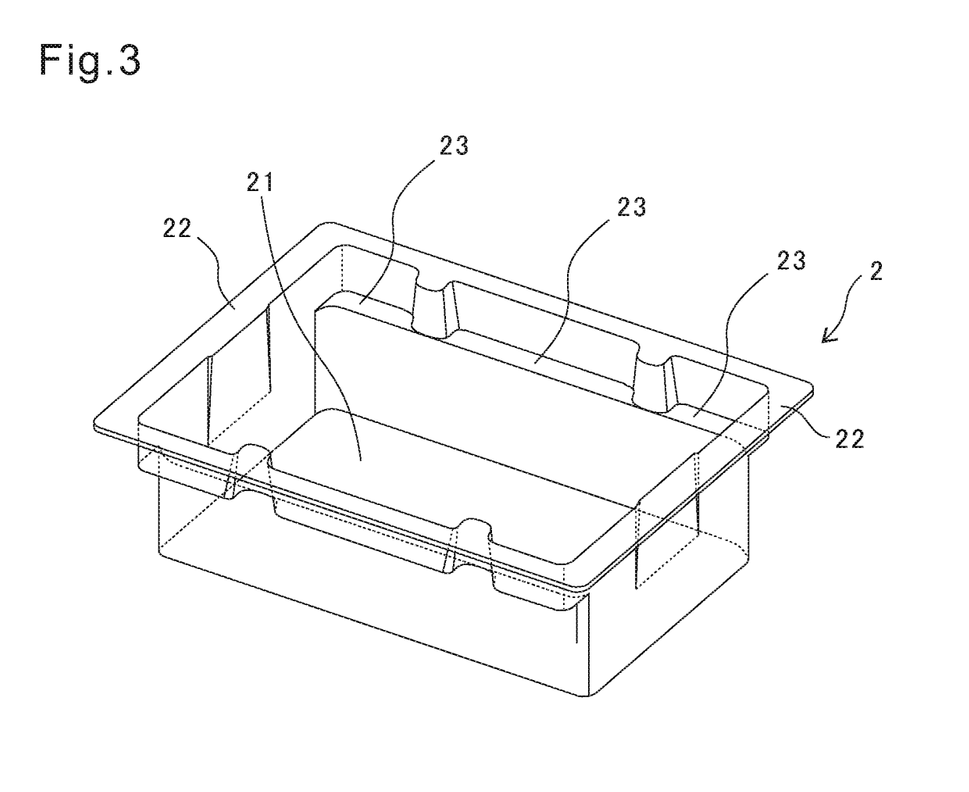
FIG. 3 shows a perspective view of a container body in the medical device container shown in FIG. 1.

As shown in FIG. 3, the container body 2 is formed in a box (basket) shape having a planar shape of nearly rectangle, and comprises a circular flange portion 22 which is formed at the upper opening portion to extend circularly and outward and a pair of uneven portions 23 which are formed in a longitudinal direction of the container body 2 which are positioned a predetermined length lower than the circular flange portion 22. The uneven portion may be formed in a circular shape. The planar shape of the container body 2 may be a polygonal shape, a circular shape or an oval shape, other than the nearly rectangular shape shown in the drawings. The container body 2 is formed by synthetic resin, metal or various composites of these materials.

Figure 4A:
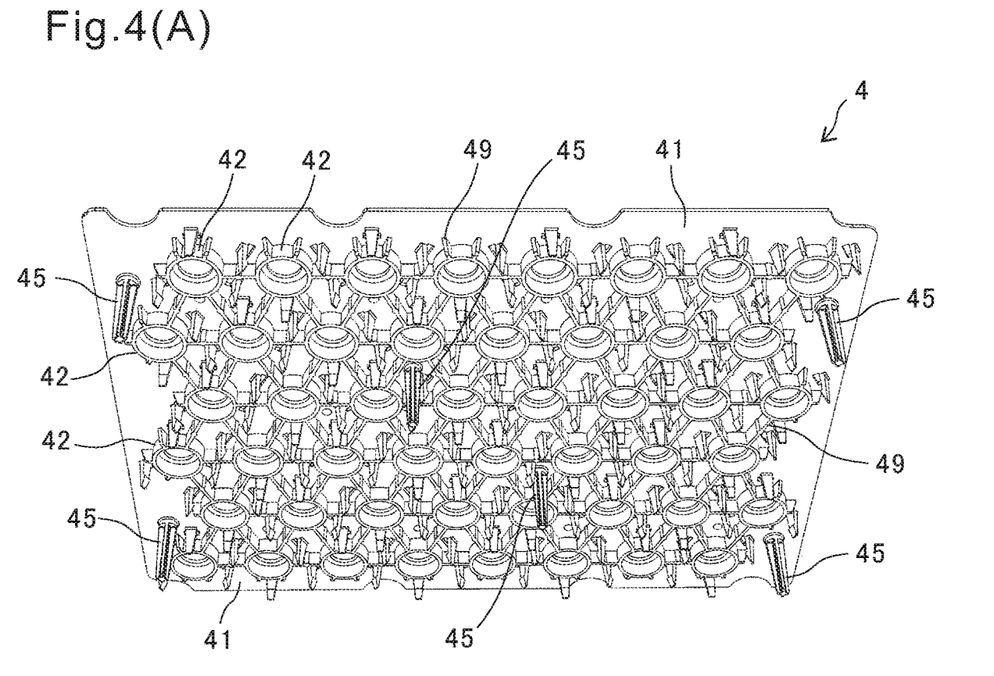
FIG. 4(A) shows a perspective view of a holder which is housed in the medical device container shown in FIG. 1; and (B) shows a plan view of the holder shown in (A).
Figure 4B:
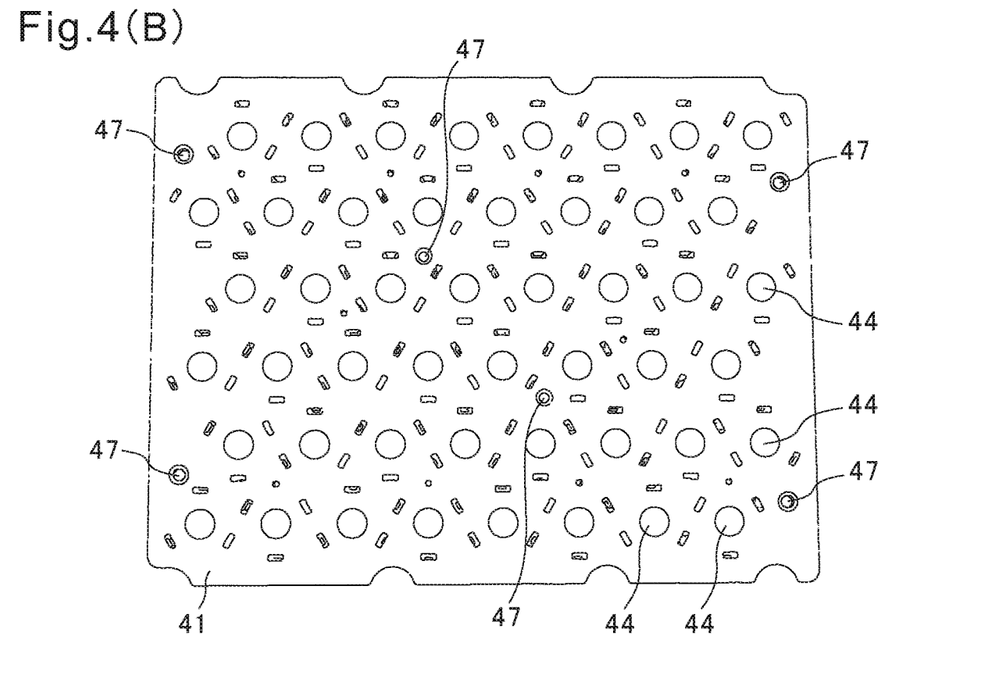

A medical device holder 4 is placed alone inside the container body 2 or plural medical device holders 4 are stacked and placed in the container body 2 as shown in FIG. 2(B) to house the medical device holder 4 in the container body 2. As shown in FIG. 4(A) (B) and FIG. 5(A) (B), the medical device holder 4, which is to be housed in the container body 2, comprises a plate-like basal plate portion 41 and plural tubular portions 42 protruding downward from the basal plate portion 41. A plate-like stay 49 is positioned to extend from the outside of a tubular portion 42 to the outside of an adjacent tubular portion 42. A circular flange portion 421 is formed on a base end portion (the side of the basal plate portion 41) of the tubular portion 42 to extend in a radial direction inside the tubular portion 42.

Figure 5:
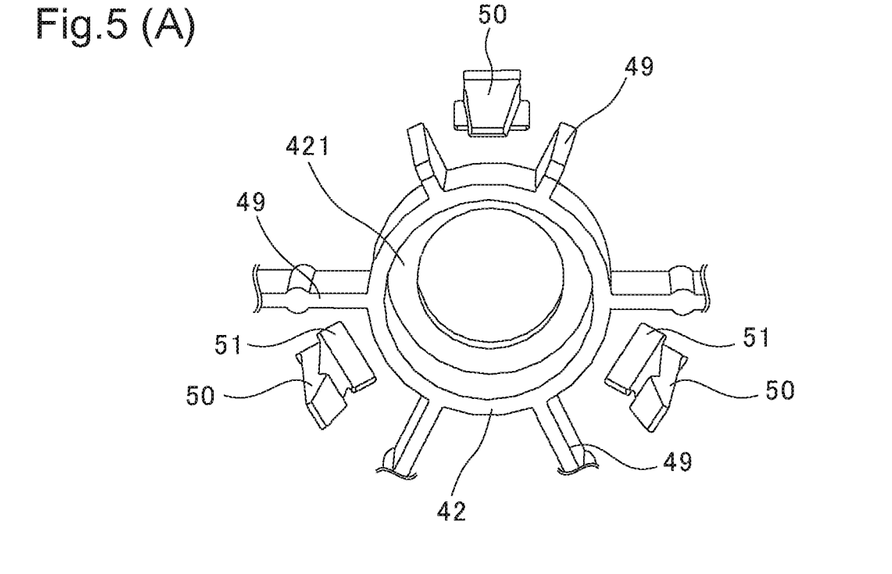
Figure 5B:
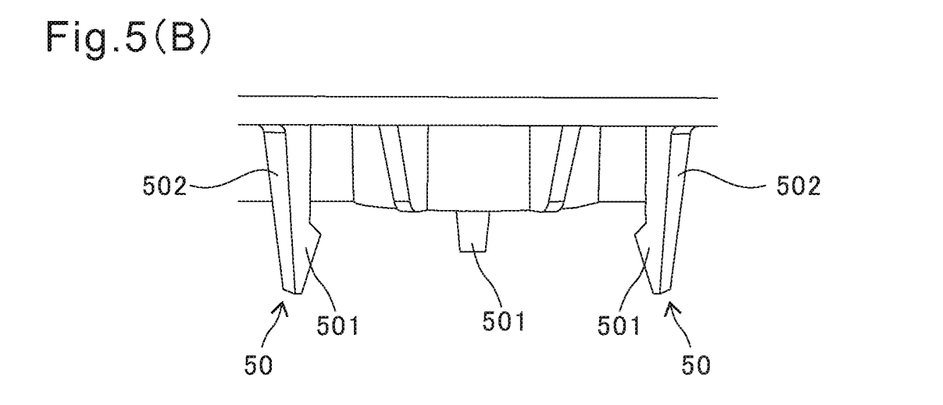

As shown in FIG. 5(A) (B), a locking projection 50 protruding downward is formed in the circumference of the tubular portion 42. The locking projection 50 is constituted by a columnar leg portion 502 and a locking claw 501 which protrudes toward each tubular portion 42. In this example, three locking projections 50 are formed in the circumference of each tubular portion 42 respectively, however the number of the locking projections 50 is not limited to three and it may be two, four or more. A nearly rectangular pass-through slot 51 is formed between the base end portion of the locking projection 50 and the tubular portion 42. The shape of the pass-through slot 51 is not limited to the shape shown in the drawings, and it may be a triangle shape, an oval shape, a circular shape or a polygonal shape. The position of the pass-through slot 51 is not limited to the area between the base end portion of the locking projection 50 and the tubular portion 42, and it may be any neighborhood of the tubular portion 42. By forming the pass-through slot 51, a sterilization fluid effectively coats the interior portion of the container.

As shown in FIG. 4(A), the medical device holder 4 comprises a support rod 45 protruding downward from the basal plate portion 41 in a peripheral portion and a central portion. A support rod 45 is longer than the tubular portion 42 and the locking projection 50, and therefore a medical device (cap 62) and the like, which is stored in the locking projection 50 and the tubular portion 42, does not contact the bottom surface of the container body 2. In a condition where the medical device holders 4 are stacked, medical devices (caps 62) and the like, which are stored in the locking projections 50 and the tubular portions 42, do not contact the neighboring holders.

In order to stack the holders 4, the lower end portion (tip portion) of the support rod 45 is inserted in a connecting hole 47 (the upper surface side of the basal plate portion 41) on the base end portion of the support rod 45 of the holder 4 which was placed previously. The stacked condition shown in FIG. 2 (B) is obtained by repeating this operation sequentially.

Figure 5C:
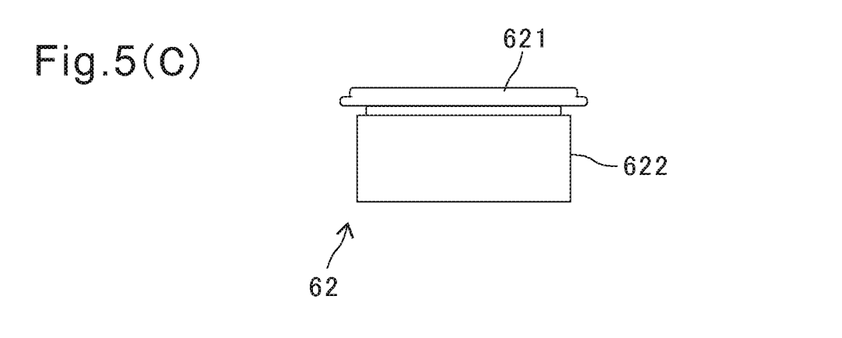

By referring to FIG. 5 (A) through (C), a way of storing a cap 62 as one example of medical devices in the holder 4 will be explained. A rubber plug (not shown in the drawings) is fitted in the opening portion of a medicine container or the like. The cap 62 is used to cover the rubber plug in order to prevent the rubber plug from being detached. The cap 62 comprises a top panel 621 and a skirt 622 which protrudes tubularly from the rear side of the top panel 621. When the cap 62 is moved by facing the top panel 621 to the tubular portion 42, an outer edge of the top panel 621 contacts the locking claw 501 of the locking projection 50. When the cap 62 is further compressed, the locking projection 50 is deformed elastically, the top panel 621 passes through the locking claw 501 and contacts the tubular portion 42. The cap 62 is held in the holder 4 when the locking claw 501 covers the top panel 621 by elastic return. The holder 4 is suitable to hold a rubber plug (not shown in the drawings) and the like which is to seal the opening of a medicine container and the like. It is also suitable to hold the cap 62 incorporating a rubber plug.

Although the above-mentioned holder 4 is for holding the cap 62, the holder 4 may have various other shapes depending upon a type of medical device to be held, like a piston, a barrel, or vial. Although the gas non-permeable film 3, which will be described later, contacts the basal plate portion 41 in a holder 4 for holding the cap 62 or a piston (not shown in the drawings). It does not contact the basal plate portion 41 but contacts a medical device like a barrel or a vial in case of a holder for holding a medical device like a barrel or a vial. There are cases where a gas non-permeable film 3 may contact both the basal plate portion 41 and a medical device depending upon a type of the holder 4.

Figure 6:
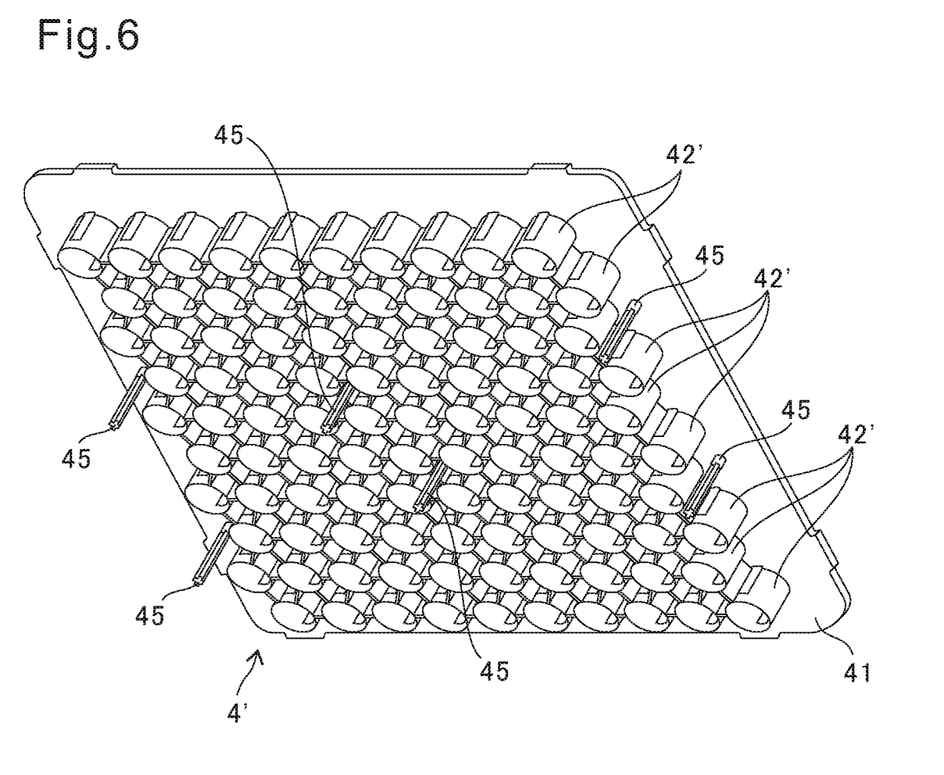
FIG. 6 shows a perspective view of another example of a holder which is housed in the medical device container shown in FIG. 1.
Figure 7A:
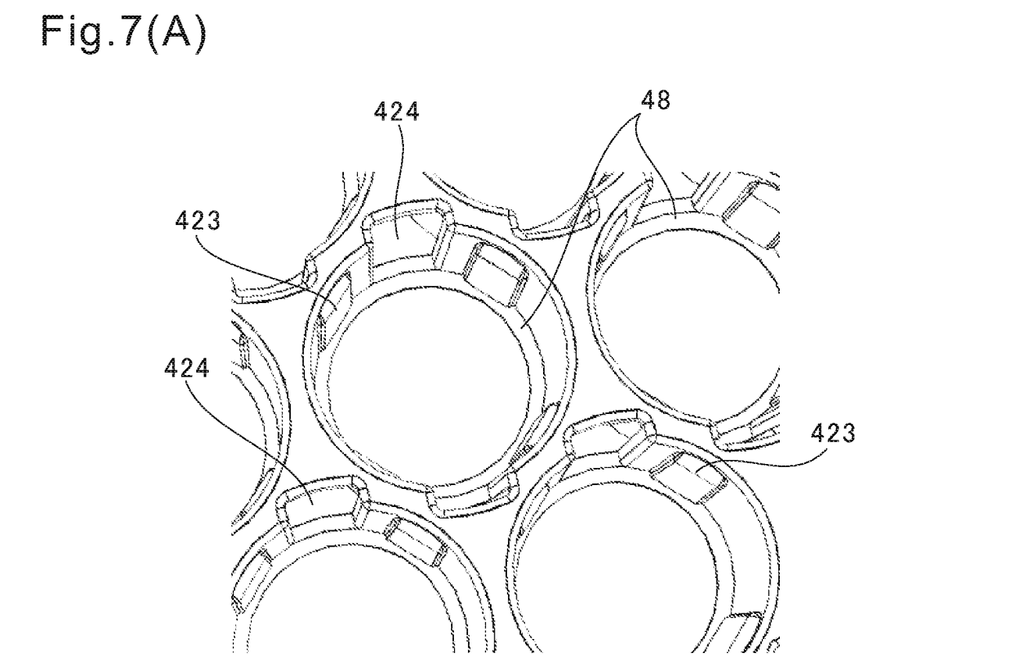
Figure 7B:
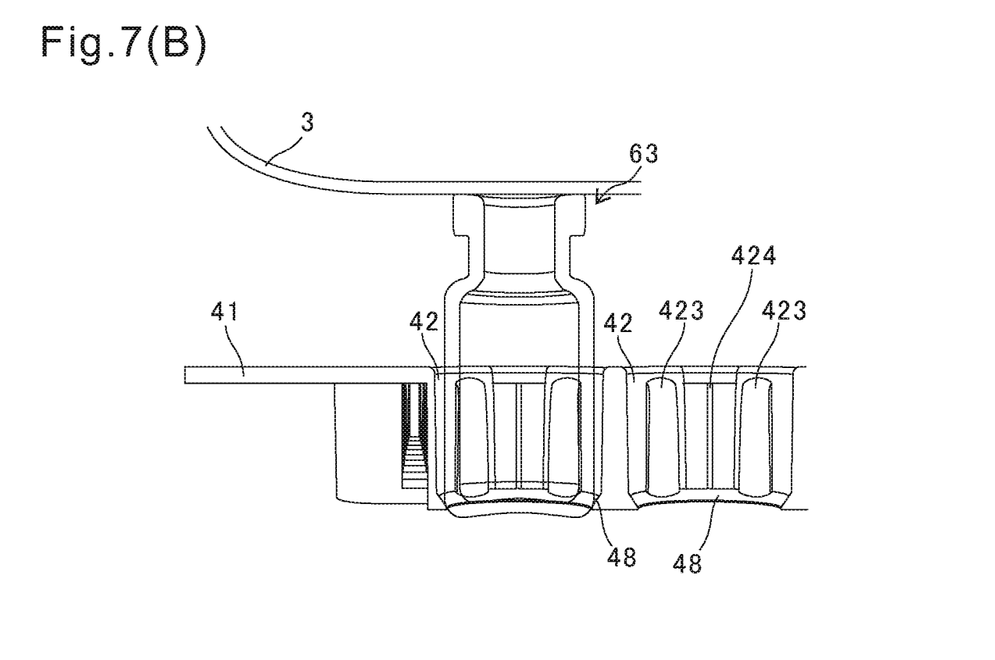

Next, a holder 4' for holding a vial 63 will be explained. As shown in FIG. 6 and FIG. 7(A) (B), a circular convex portion 48 is formed at the bottom end on the inner side surface of the tubular portion 42'. Plural plate-like pads 423 having a cross-section shape of a nearly rectangle on the inner side surface of the tubular portion 42'. Although four pads are positioned at equal spaces in FIG. 7(A) (B), it is not limited to this arrangement, and it may as well have two or more pads and they do not need to be positioned at equal spaces. The pads may as well have a cross-section shape like a circle, an oval, a polygon and the like, other than a rectangle. The shape of the pad 423 is not limited to plate-like, and it may as well have a dome-like shape having a certain thickness. Plural air holes 424 are formed at the tubular portion 42'. The shape of the air hole 424 may be nearly rectangular as shown in the drawings, circular, oval or polygonal, and it is preferable to make the air hole 424 communicate with the basal plate portion 41'. It enables to coat the structure efficiently by a sterilization fluid. Other elements are identical to those of the holder 4. By having such a structure of the holder 4', even when the holders 4' are stacked, it is possible to conduct an assured sterilization process and it is possible to conduct a sterilization of a number of medical devices at one time.

The basal plate portion 41 is especially suitable to hold a medical device like a vial 63 as shown in FIG. 7(B). It is possible to fix the top surface of a medical device like the vial 63 by pressing the top surface with the gas non-permeable film 3 and prevent the vial 63 from wobbling by further supporting the side surface of the vial 63 and the like with the pad 423. It is also possible to coat the vial 63 with a sterilization fluid by keeping a gap between the vial 63 and the tubular portion 42. The air hole 424 also functions to coat the vial 63 efficiently with a sterilization fluid.

A way for housing the vial 63 as one example of a medical device in the holder 4' shown in FIG. 6 and FIG. 7(A) (B) will be explained. The vial 63 is housed and held in the holder 4' by inserting the bottom of the vial 63 in the opening portion (the side of the basal plate portion 41) which is positioned above the tubular portion 42, contacting the circumferential portion of the bottom surface of the vial 63 with the circular convex portion 48 and contacting the side surface of the vial 63 with the pad 423.

As shown in FIG. 1 and FIG. 2(A) (B), the gas non-permeable film 3 seals the circular flange portion 22 of the container body 2 by heat welding and the like such that it can be peeled, and then seals the opening portion at the upper portion of the container body 2. As the gas non-permeable film 3, a film made of polyethylene, polyethylene terephthalate, polyvinylidene chloride or a stacked film of these films and the like. For example, it is possible to use a film made by staking a polyethylene film, a polyethylene terephthalate film below the polyethylene film and an adhesive film below the polyethylene terephthalate film. The gas non-permeable film 3 may be made of a gas non-permeable film and a "Tyvek and the like" sheet which is stacked on the gas non-permeable film 3, where the gas non-permeable film 3 does not pass gas, steam, bacteria and others through it, and the "Tyvek and the like" sheet is positioned on the side contacting the container body 2. It is possible to reduce the material because only the opening portion of the container body 2 is covered as opposed to vacuum bag packaging where the whole medical device container 1 is covered. As the opening portion is covered by the gas non-permeable film 3, it is possible to sterilize the exterior package of the medical device container 1.

The internal pressure of the medical device container 1 is in a condition of reducing the pressure to a value less than the atmospheric air pressure. Because of this operation, as shown in FIG. 2 (B), the gas non-permeable film 3 dents toward the inner side of the medical device container 1 and contacts the basal plate portion 41 of the holder 4.

Therefore, the holder 4 is fixed by the gas non-permeable film 3. When a medical device container is sterilized by radioactive ray, the effect of the radioactive ray sterilization is enhanced because the amount of the internal gaseous matter is small.

Although it is sufficient to set the internal pressure of the medical device container 1 a value less than the atmospheric air pressure, it is preferable to set the internal pressure to 400 hectopascal (hPa) or higher and less than 1013 hectopascal (hPa) because there is no possibility of degradation of cleanliness and no possibility of damage of the gas non-permeable film 3 by a deformation of the holder 4, and it is possible to effectively fix the holder during transportation. Even when the gas non-permeable film 3 does not contact the basal plate portion 41 of the holder 4, it is sufficient that the gas non-permeable film 3 dents to reach the neighborhood of the basal plate portion 41 of the holder 4. It is because that the holder 4 is kept in a fixed condition where it is almost impossible to move the holder 4. In case of the holder 4' for supporting the vial 63, as shown in FIG. 7(B), the gas non-permeable film 3 contacts the vial 63 (medical device). Other structures are identical to those of the holder 4.

Figure 8:
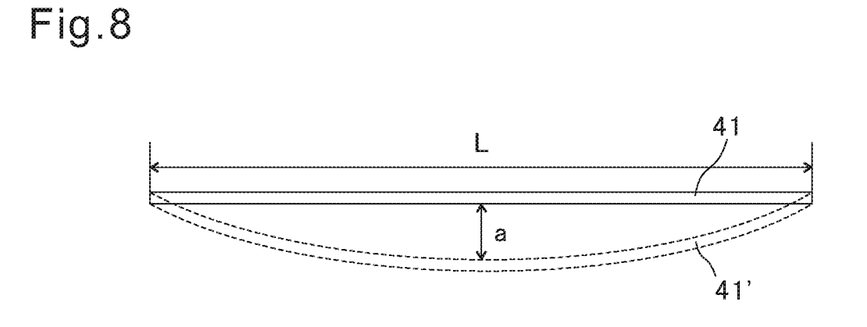
FIG. 8 shows a side view of a basal plate portion in a longitudinal direction showing the conditions before and after the deformation by pressure reduction.

FIG. 8 is a side view of the basal plate portion 41 of the holder 4 in a longitudinal direction showing conditions before and after a deformation by pressure reduction, and the elements including the tubular portion 42 other than the basal plate portion 41 are omitted. As shown in FIG. 8, although the basal plate portion 41 of the holder 4 is nearly flat plate shaped before the pressure reduction, it is dented downward and deformed to the basal plate portion 41' as shown by the dotted line when the gas non-permeable film 3 contacts it by pressure reduction. The maximum displacement by this operation is represented by a. If the displacement is large, there is a possibility of degradation of cleanliness by a friction and the like between the contents in a process of a displacement of the holder 4. There is also a possibility of a detraction of the functions for positioning the medical device, holding the medical device and the like, which are the inherent roles of the holder 4, and there is a possibility of an interference or a drop of the medical devices.

Therefore, it is preferable to set the ratio ($\alpha$/L) to $0 < \alpha/L \leq 0.15$, where L is the longitudinal length of the basal plate portion 41 of the holder 4, and a is the maximum displacement of the basal plate portion 41 of the holder 4 in a vertical direction toward the bottom surface of the container body 2.

Next, a process for producing the medical device container 1 will be explained. First, the holder 4 is placed alone inside the container body 2 or plural medical device holders 4 are stacked and placed in the container body 2 as shown in FIG. 2(B). After this operation, in a space where the pressure is reduced to a value less than the atmospheric air pressure, a gas non-permeable film 3 in a long rolled condition, for example, is used to cover and wrap the whole opening portion (including the circular flange portion 22) of the container body 2, and then the gas non-permeable film 3 is cut in an appropriate length at the same time as heat welding by contacting a heat source with a portion where the gas non-permeable film 3 contacts the circular flange portion 22. The gas non-permeable film 3 may be cut after the heat welding. By this process, the internal pressure of the medical device container 1 can be less than the atmospheric air pressure. The process for reducing the pressure and heat welding the gas non-permeable film 3 may be automatically performed by a chamber type pack sealer machine (not shown in the drawing). By this operation, because it is sealed by the gas non-permeable film 3 under a reduced pressure, variations in the pressure reduction condition by operators can be eliminated.

When the medical device container 1, which is produced under a reduced pressure by the previously explained process, is put in the atmospheric air pressure, the gas non-permeable film 3 bents toward the inner side of the medical device container 1 as shown in FIG. 2(B).

As another embodiment, it is possible to dent the gas non-permeable film 3 toward the inner side of the medical device container 1 by reducing the inner pressure of the medical device container 1 through an opening portion formed on the side surface portion or the bottom surface portion of the container body 2 after sealing the gas non-permeable film 3 under ordinary pressure.

Figure 9A:
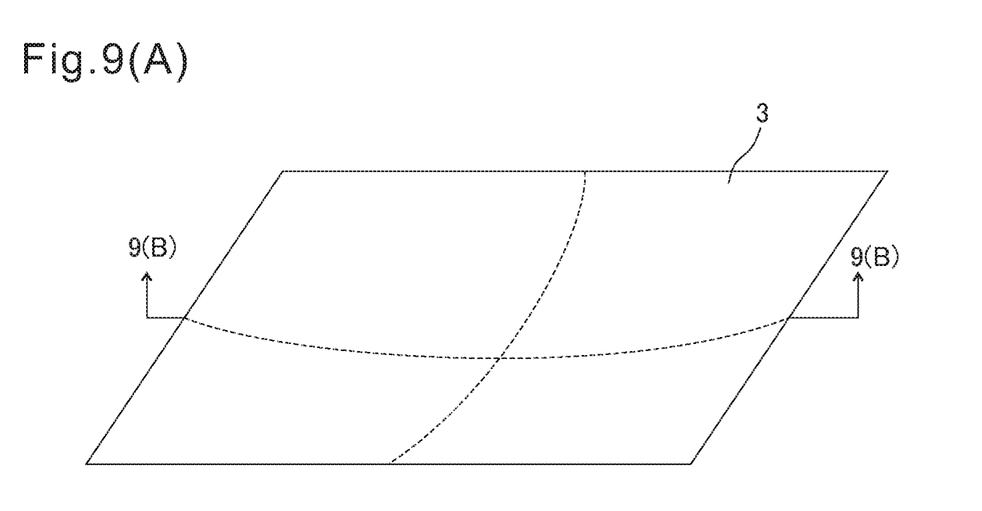
Figure 9B:
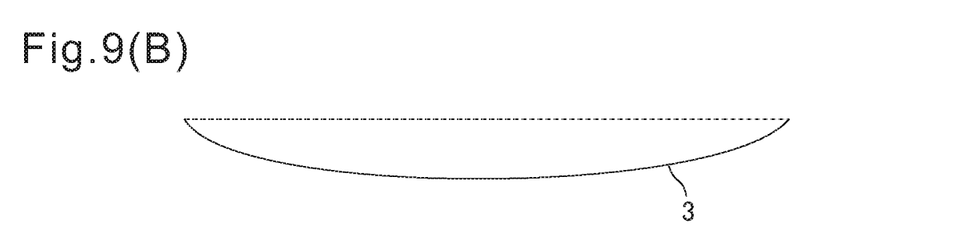

Alternatively, it is possible to seal the circular flange portion 22 with the gas non-permeable film 3 in a downwardly dented condition from the beginning in a space where the pressure is reduced to a value less than the atmospheric air pressure as shown in FIG. 9(A) (B). According to this process, a material which is hardly elongated can be used as the gas non-permeable film 3, or the reduction in the thickness of the gas non-permeable film 3 by stretching can be diminished. It is preferable to set the ratio (M1/M2) to $0.70 \leq (M1/M2) \leq 0.99$, where M1 is the area of the opening portion (including the circular flange portion 22) of the container body 2 before the pressure reduction (41 corresponds to xy, where x is the length in a longitudinal direction and y is the length in a short direction according to the example shown in FIG. 2), and M2 is the surface area of the gas non-permeable film 3 before the pressure reduction. It is not preferable for fixing the holder 4 if this ratio is set to a value which is too small because a crease appears on the gas non-permeable film 3. It is preferable to set $(M1/M2) \leq 0.90$ in view of a sag of the gas non-permeable film 3.

EXPLANATION OF REFERENCES 1 medical device container
2 container body
21 container bottom portion
22 circular flange portion
23 uneven portion
3 gas non-permeable film
4 4' holder
41 41' basal plate portion
42 42' tubular portion
421 circular flange portion of tubular portion
423 pad
424 air hole
45 support rod
47 connecting hole
48 circular convex portion
49 stay
50 locking projection
501 locking claw
502 leg portion
51 pass-through slot
62 cap
621 top plate
622 skirt
63 vial

The invention claimed is:

1. A medical device container, comprising:
   a container body having an opening portion at an upper portion;
   a holder placed in the container body and including
      a basal plate portion,
      a plurality of tubular portions protruding from the basal portion,
      a plurality of holding portions, each of the plurality of holding portions being formed on the basal plate portion and adapted to hold a medical device, and
      a plurality of stays, each of the plurality of stays extending between two of the plurality of tubular portions adjacent to each other; and
   a gas non-permeable film sealing the opening portion,
   wherein an internal pressure of the medical device container is less than an atmospheric air pressure,
   each of the plurality of holding portions includes locking projections, each of the locking projections protruding farther than the plurality of tubular portions and the plurality of stays from the basal plate portion between two of the plurality of stays and having a locking claw protruding inwardly toward each of the plurality of tubular portions at one end thereof, and
   the basal plate portion includes slots, each of the slots being formed inside each of the locking projections.

2. A medical device container according to claim 1, wherein the gas non-permeable film contacts at least one of the medical device and the holder.

3. A medical device container according to claim 1, wherein a ratio ($\alpha$/L) is set to $0<\alpha/L \leq 0.15$, where L is a longitudinal length of the basal plate portion of the holder, and $\alpha$ is a maximum displacement of the basal plate portion of the holder in a vertical direction toward a bottom surface of the container body.

4. A medical device container according to claim 1, wherein a ratio (M1/M2) is set to $0.70 \leq (M1/M2) \leq 0.99$, where M1 is an area of the opening portion of the container body before a pressure reduction, and M2 is an area of the gas non-permeable film which seals the opening portion before the pressure reduction.

5. A medical device container structure, comprising:
   the medical device container according to claim 1; and
   the medical device including a cap covering one end of the medical device and held with the locking claw of each of the locking projections.

6. A medical device container structure according to claim 5, wherein the cap includes a top panel and a skirt protruding tubularly from one end of the top panel, the top panel circumferentially protruding from the skirt to be held with the locking projections, and
   the holder further includes a plurality of side rods protruding from the basal plate portion, each of the plurality of side rods having a length longer than those of the locking projections, and the basal plate portion includes a plurality of connecting holes into which the plurality of side rods is inserted, such that the medical device does not contact a bottom surface of the container body or another basal plate portion of another holder placed under the holder.

7. A medical device container according to claim 1, wherein the plurality of stays includes six stays radially extending from each of the plurality of tubular portions to form six spaces around each of the plurality of tubular portions, and the locking projections include three projections alternately arranged in the six spaces.

8. A medical device container, comprising:
a container body having an opening portion at an upper portion;
a holder placed in the container body and including
a basal plate portion,
a plurality of tubular portions protruding from the basal portion, and
a plurality of holding portions, each of the plurality of holding portions being formed on each of the plurality of tubular portions and adapted to hold a medical device; and
a gas non-permeable film sealing the opening portion,
wherein an internal pressure of the medical device container is less than an atmospheric air pressure,
each of the plurality of tubular portions includes at least one pad protruding inwardly from an inner surface of each of the plurality of tubular portions, and at least one air hole formed on the inner surface of each of the plurality of tubular portions, and
each of the plurality of holding portions includes a convex portion protruding inwardly from the inner surface of each of the plurality of tubular portions at a bottom end thereof and adapted to hold the medical device.

9. A medical device container according to claim 8, wherein the holder further includes a plurality of side rods protruding from the basal portion, each of the plurality of side rods having a length longer than those of the plurality of tubular portions, and the basal plate portion includes a plurality of connecting holes into which the plurality of side rods is inserted, such that the medical device does not contact a bottom surface of the container body or another basal plate portion of another holder placed under the holder.

10. A medical device container according to claim 8, wherein the at least one pad includes four pads arranged at equal intervals along the inner surface of each of the plurality of tubular portions, and the at least one air hole includes two air holes facing each other in each of the plurality of tubular portions.

11. A medical device container according to claim 8, wherein the gas non-permeable film contacts at least one of the medical device and the holder.

12. A medical device container according to claim 8, wherein a ratio ($\alpha/L$) is set to $0<\alpha/L\leq0.15$, where L is a longitudinal length of the basal plate portion of the holder, and $\alpha$ is a maximum displacement of the basal plate portion of the holder in a vertical direction toward a bottom surface of the container body.

13. A medical device container according to claim 8, wherein a ratio (M1/M2) is set to $0.70\leq(M1/M2)\leq0.99$, where M1 is an area of the opening portion of the container body before a pressure reduction, and M2 is an area of the gas non-permeable film which seals the opening portion before the pressure reduction.

* * * * *